(12) United States Patent
Ye et al.

(10) Patent No.: US 9,295,480 B2
(45) Date of Patent: Mar. 29, 2016

(54) CRANIOTOMY DRILL

(75) Inventors: Lei Ye, Chongqing (CN); Jian Zhou, Chongqing (CN); Hua Feng, Chongqing (CN); Fei Li, Chongqing (CN); Hengyang Zhu, Chongqing (CN); Congxiao Li, Chongqing (CN)

(73) Assignee: CHONGQING RUNZE PHARMACEUTICAL CO., LTD., Chongqing (CN)

( * ) Notice: Subject to any disclaimer, the term of this patent is extended or adjusted under 35 U.S.C. 154(b) by 494 days.

(21) Appl. No.: 13/823,077

(22) PCT Filed: Aug. 24, 2011

(86) PCT No.: PCT/CN2011/078827
§ 371 (c)(1),
(2), (4) Date: Mar. 13, 2013

(87) PCT Pub. No.: WO2012/041135
PCT Pub. Date: Apr. 5, 2012

(65) Prior Publication Data
US 2013/0178856 A1 Jul. 11, 2013

(30) Foreign Application Priority Data

Sep. 30, 2010 (CN) .......................... 2010 1 0298084

(51) Int. Cl.
*A61B 17/16* (2006.01)

(52) U.S. Cl.
CPC ........... *A61B 17/1695* (2013.01); *A61B 17/162* (2013.01); *A61B 17/1628* (2013.01); *A61B 17/1626* (2013.01)

(58) Field of Classification Search
CPC .... B25F 5/001; A61B 17/16; A61B 17/1633; A61B 17/1628
USPC ......................................................... 173/217
See application file for complete search history.

(56) References Cited

U.S. PATENT DOCUMENTS

| | | | | |
|---|---|---|---|---|
| 3,709,630 A | * | 1/1973 | Pohl | A61B 17/1628 173/218 |
| 3,734,207 A | * | 5/1973 | Fishbein | A61B 17/1622 173/217 |
| 4,199,160 A | * | 4/1980 | Bent | A61C 1/14 279/30 |
| 4,692,073 A | * | 9/1987 | Martindell | B23B 31/1071 279/75 |
| 5,490,683 A | * | 2/1996 | Mickel | A61B 17/162 279/75 |
| 5,505,737 A | * | 4/1996 | Gosselin | A61B 17/32002 279/75 |
| 6,062,575 A | * | 5/2000 | Mickel | A61B 17/162 279/75 |
| 6,270,087 B1 | * | 8/2001 | Mickel | A61B 17/162 279/75 |
| 6,554,290 B2 | * | 4/2003 | Lin | B23B 31/22 279/72 |
| 6,966,391 B2 | * | 11/2005 | Tang | B25F 5/001 173/216 |
| 2003/0136134 A1 | * | 7/2003 | Pun | F24F 5/0035 62/91 |
| 2005/0116429 A1 | * | 6/2005 | Chang | B25B 15/001 279/75 |
| 2008/0077149 A1 | * | 3/2008 | Hoegerle | A61B 17/1613 606/80 |

\* cited by examiner

*Primary Examiner* — Gloria R Weeks

(57) ABSTRACT

A craniotomy drill includes a main machine, a retarder and a locking seat. A drill transmission rod connected to the output shaft of the retarder is inserted in the locking seat. The main machine comprises a handle at the lower portion and an accommodating part at the upper portion, with a stator and a rotor of a DC electric motor being provided inside the accommodating part and a wall of the accommodating part being the stator housing of the DC electric motor. This craniotomy drill has a simple structure with the wall of the accommodating part as the stator housing of the electric motor, such that the volume and the weight are reduced. It is safe in use without the risk of the electric motor sliding out. By utilizing materials and processes of water resistant technology and an integrative design, a relatively good water resistant performance is achieved.

7 Claims, 4 Drawing Sheets

CRANIOTOMY DRILL

BACKGROUND OF THE INVENTION

1. Field of the Invention

The present invention relates to a bone drill machine for surgery.

2. Description of the Prior Art

During a surgical operation, a craniotomy drill is often used to open a skull. The craniotomy drill comprises a main machine, a retarder, a locking seat and a drill bit. The main machine comprises a handle at a lower part thereof and a casing having a cylindrical accommodating part and a cylindrical electric motor at an upper part thereof. To assemble the craniotomy drill, the electric motor is placed in the chamber of the cylindrical accommodating part at the upper part of the casing, and then the electric motor is secured with screws. This structure has a large-size upper part of the casing and the whole weight of the craniotomy drill is heavy. After a period of time to use, the screws may loosen and the electric motor may slip off from the accommodation room to cause an accident during surgery.

Accordingly, the inventor of the present invention has devoted himself based on his many years of practical experiences to solve these problems.

SUMMARY OF THE INVENTION

The primary object of the present invention is to provide a compact and light craniotomy drill.

In order to achieve the aforesaid object, the craniotomy drill comprises a main machine, a retarder and a locking seat which are successively threadedly connected. A drill transmission rod connected to an output shaft of the retarder is inserted in the locking seat. The main machine comprises a handle at a lower portion thereof and an accommodating part at an upper portion thereof. A stator and a rotor of a direct current (DC) electric motor are provided inside the accommodating part and a wall of the accommodating part is as a stator housing of the DC electric motor.

For convenient disassembly of the drill transmission rod, the locking seat comprises a boss with a through hole, a bearing arranged on an inner wall of a small cylinder on the boss, a support member to support the bearing and a locking sleeve fitted on the boss. The locking sleeve has a first bugle arranged on an upper part of an inner wall of the locking sleeve and a second bugle arranged on a lower part of the inner wall of the locking sleeve. A spring is provided between the second bugle and an upper bottom face of the boss. A press plate is threadedly connected to an outer wall of the top part of the small cylinder on the boss and presses the first bugle. Holes of different sizes are arranged on the inner wall of the small cylinder and the support member corresponding in position to the second bulge to form a stepped hole. A steel ball is arranged in the stepped hole.

For fixation of the bearing, the upper bottom face is threadedly connected with the tightening member to hold against the bearing and the support member.

For stable running of the drill transmission rod, the locking seat comprises two bearings respectively located under the outer wall and above the tightening member.

For convenient connection of the retarder, an inner wall of a big cylinder under the boss has inner threads.

For guiding the conductive wire of the stator, the rear part of the accommodating part is provided with a stop plate having a hole. A rear end cap is threadedly connected to the rear end of the accommodating part. The stator of the DC electric motor has a conductive wire. The conductive wire passes the hole of the stop plate to enter the handle.

For waterproofing, the conductive wire of the stator of the DC electric motor is provided with waterproof layer.

For seal of the retarder, the output axle of the retarder is provided with a lip-type packing.

The present invention has a simple structure with the wall of the accommodating part as the stator housing of the electric motor, such that the volume and the weight are reduced. It is safe in use without the risk of the electric motor sliding out. By utilizing materials and processes of water resistant technology and an integrative design, a relatively good water resistant performance is achieved. When it is necessary to insert the drill transmission rod, the locking sleeve is pressed down. At this moment, the second bugle disengages from the steel ball. The steel ball meets the drill transmission rod to roll outward. After the drill transmission rod reaches a desired position, the locking sleeve is released. Through the spring, the locking sleeve ascends and the second bugle holds against the steel ball to move inward to engage with the recess of the drill transmission rod in order to position the drill transmission rod. The drill head locking apparatus and the drill head are easy and convenient to operate, lock firmly, and offer an improved safety.

DETAILED DESCRIPTION OF THE PREFERRED EMBODIMENTS

Embodiments of the present invention will now be described, by way of example only, with reference to the accompanying drawings.

Figure 1:
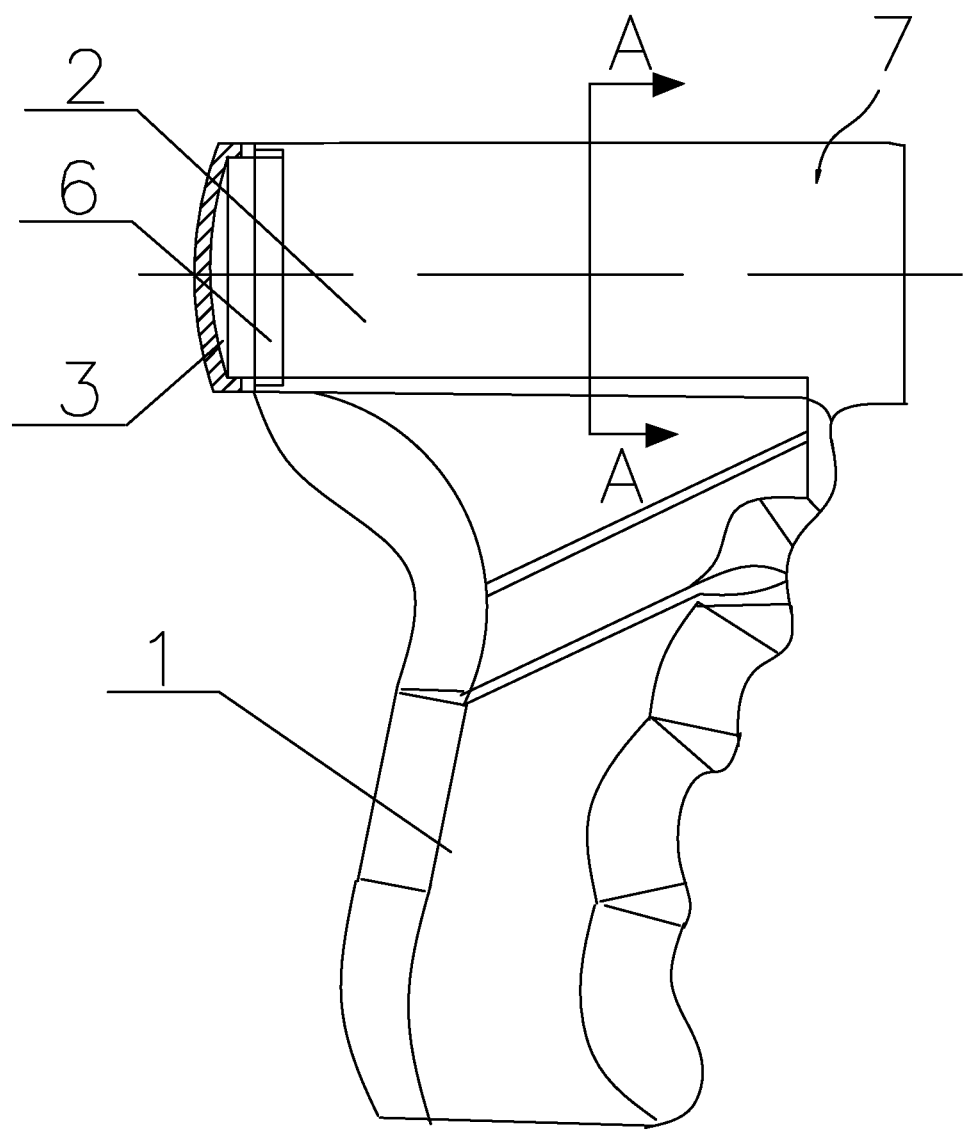
FIG. 1 is a schematic view showing the main machine according to a preferred embodiment of the present invention.
Figure 2:
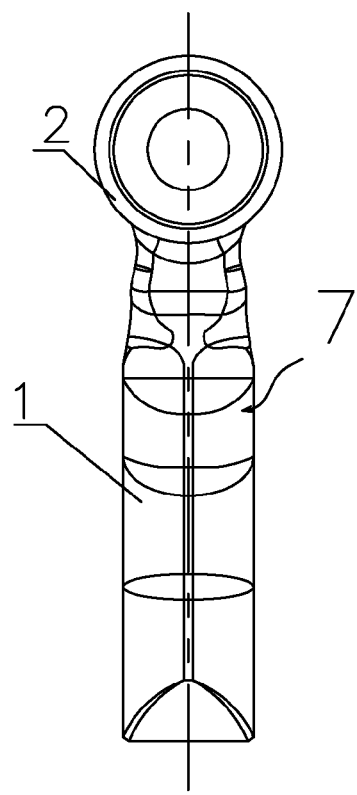
FIG. 2 is a right side view of FIG. 1.
Figure 3:
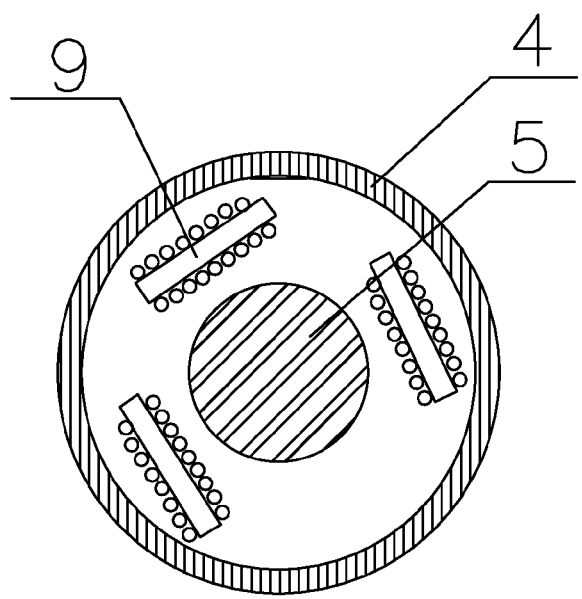
FIG. 3 is a sectional view taken along line A-A of FIG. 1.
Figure 4:
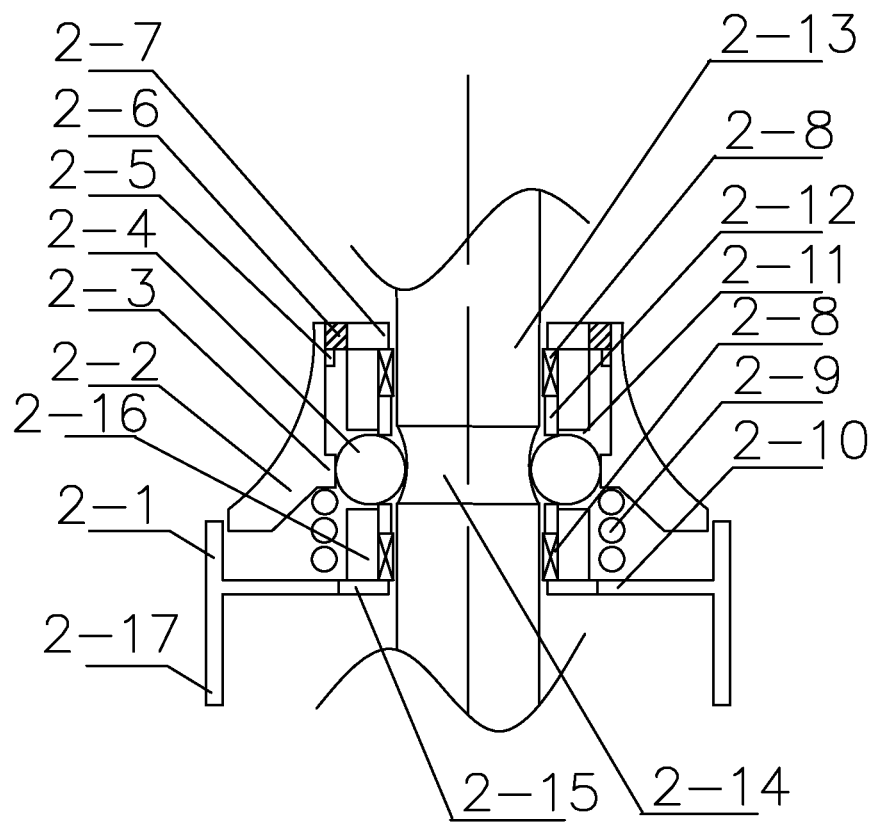
FIG. 4 is a sectional view showing the locking seat according to the preferred embodiment of the present invention.
Figure 5:
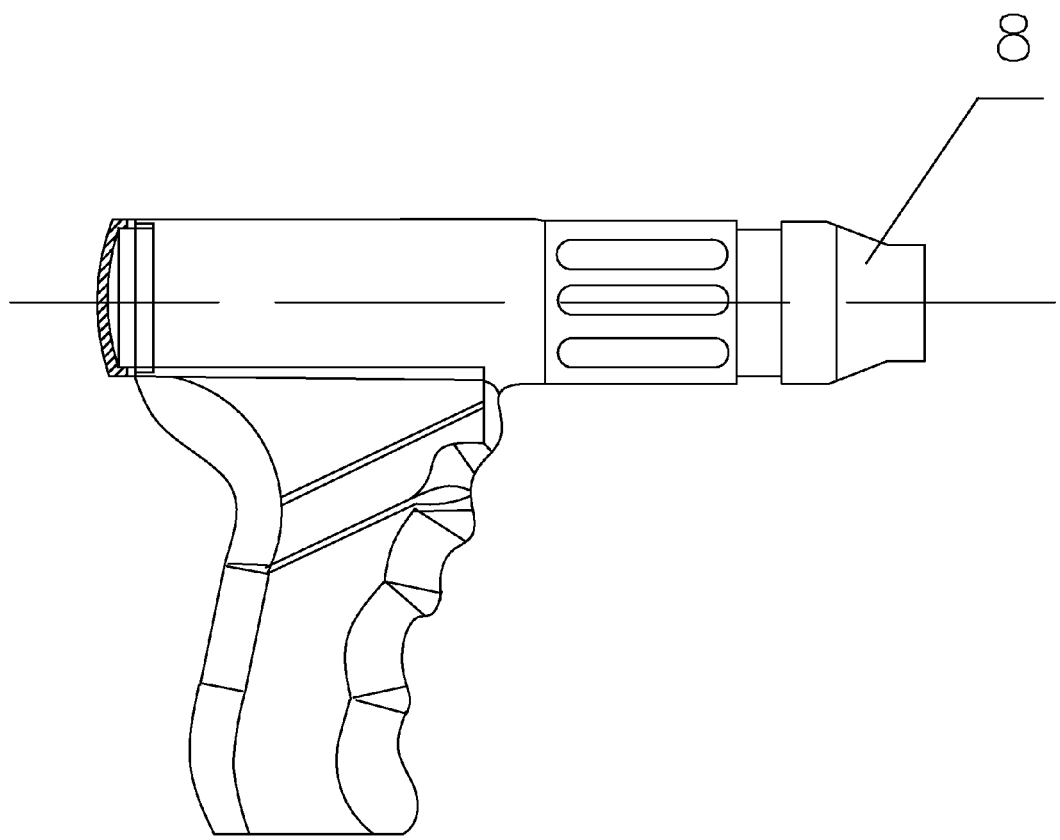
FIG. 5 is a schematic view of the preferred embodiment of the present invention.

As shown in FIG. 1 to FIG. 2, a craniotomy drill comprises a main machine, a retarder and a locking seat which are successively threadedly connected. A drill transmission rod connected to an output shaft of the retarder is inserted in the locking seat. The main machine comprises a handle (1) at a lower portion thereof and an accommodating part (2) at an upper portion thereof. A stator and a rotor of a direct current (DC) electric motor are provided inside the accommodating part (2) and a wall (4) of the accommodating part (2) is as a stator housing of the DC electric motor. A rear part of the accommodating part (2) is provided with a stop plate (6) having a hole to divide the accommodating part (2) into two chambers. The stator of the motor is disposed in the front chamber. A rear end cap (3) is threadedly connected to the rear end of the accommodating part (2). The stator of the DC electric motor has a conductive wire. The conductive wire passes the hole of the stop plate (6) and the rear chamber to enter the handle (1). The conductive wire of the stator of the DC electric motor is provided with a waterproof layer.

The locking seat comprises a boss (2-1) with a through hole and a bearing (2-8) arranged on an inner wall of a small cylinder on the boss (2-1). In this embodiment, the locking seat comprises two bearings (2-8) respectively located under an outer wall (2-7) and above a tightening member (2-15). A support member (2-12) is provided between the two bearings (2-8). An upper bottom face (2-10) is threadedly connected with the tightening member (2-15) to hold against the bearings (2-8) and the support member (2-12). The two bearings (2-8) can effectively ensure stability of the drill transmission rod and decrease heat when rotating. The support member (2-12) is to enhance firmness of the bearings (2-8).

A locking sleeve (2-2) is fitted on the boss (2-1). The locking sleeve (2-2) has a first bugle (2-5) arranged on an upper part of an inner wall of the locking sleeve (2-2) and a second bugle (2-3) arranged on a lower part of the inner wall of the locking sleeve (2-2). A spring (9) is provided between the second bugle (2-3) and the upper bottom face (2-10) of the boss (2-1). A press plate (2-6) is threadedly connected to the outer wall (2-7) of the top part of the small cylinder on the boss (2-1) and presses the first bugle (2-5). Holes of different sizes are arranged on the inner wall of the small cylinder and the support member (2-12) corresponding in position to the second bugle (2-3) to form a stepped hole (2-11). A steel ball (2-4) is arranged in the stepped hole (2-11). The hole diameter of the inner wall of the small cylinder is greater than the diameter of the steel ball (2-4), and the hole diameter of the support member (2-12) is less than the diameter of the steel ball (2-4)

The drill transmission rod (2-13) has a recess (2-14) corresponding in position to the stepped hole (2-11). An inner wall of a big cylinder under the boss (2-1) has inner threads. In this embodiment, the number of the stepped holes (2-11) and the steel balls (2-4) is two as an equivalent change. The number can be three for a better locking effect.

Although particular embodiments of the present invention have been described in detail for purposes of illustration, various modifications and enhancements may be made without departing from the spirit and scope of the present invention. Accordingly, the present invention is not to be limited except as by the appended claims.

What is claimed is:

1. A craniotomy drill, comprising a main machine (7), a retarder of conventional arts and a locking seat (8) which are successively threadedly connected, a drill transmission rod (2-13) connected to the locking seat (8), the main machine (7) comprising a handle (1) at a lower portion thereof and an accommodating part (2) at an upper portion thereof, a stator (9) and a rotor (5) of a direct current (DC) electric motor being provided inside the accommodating part (2) and a wall (4) of the accommodating part (2) enclosing the stator (9) of the DC electric motor, wherein the locking seat comprises a boss (2-1) with a through hole,
a bearing (2-8) is arranged on an inner wall of a small cylinder (2-16) on the boss (2-1),
a support member (2-12) supports the bearing (2-8) and a locking sleeve (2-2) fitted on the boss (2-1),
the locking sleeve (2-2) includes a first bulge (2-5) arranged on an upper part of an inner wall of the locking sleeve (2-2) and a second bulge (2-3) arranged on a lower part of the inner wall of the locking sleeve (2-2),
a spring (9) is provided between the second bulge (2-3) and an upper bottom face (2-10) of the boss (2-1),
a press plate (2-6) is threadedly connected to an outer wall (2-7) of a top part of the small cylinder (2-16) on the boss (2-1) and pressing the first bugle (2-5),
a stepped hole (2-11), including concentric holes of different diameters, is respectively formed by the inner wall of the small cylinder (2-16) and by the support member (2-12), corresponding in position to the second bulge (2-3); and
a steel ball (2-4) is positioned in the stepped hole (2-11).

2. The craniotomy drill as claimed in claim 1, wherein the upper bottom face (2-10) is threadedly connected with a tightening member (2-15) to hold against the bearing (2-8) and the support member (2-12).

3. The craniotomy drill as claimed in claim 2, wherein the locking seat comprises two bearings (2-8) respectively located under the outer wall (2-7) and above the tightening member (2-15).

4. The craniotomy drill as claimed in claim 3, wherein an inner wall of a big cylinder (2-17) under the boss (2-1) has inner threads.

5. The craniotomy drill as claimed in one of claims 1 and 2-4, wherein a rear part of the accommodating part (2) is provided with a stop plate (6) having a hole, a rear end cap (3) being threadedly connected to a rear end of the accommodating part (2), the stator (9) of the DC electric motor having a conductive wire, the conductive wire passing the hole of the stop plate (6) to enter the handle (1).

6. The craniotomy drill as claimed in claim 5, wherein the conductive wire of the stator of the DC electric motor is provided with a waterproof layer.

7. The craniotomy drill as claimed in claim 6, wherein the retarder is provided with a lip-type packing to connect to the drill transmission rod (2-13).

* * * * *